(12) United States Patent
Jugl et al.

(10) Patent No.: US 9,387,291 B2
(45) Date of Patent: Jul. 12, 2016

(54) DRUG DELIVERY DEVICE WITH HOUSING COMPRISING FRANGIBLE ZONE

(75) Inventors: Michael Jugl, Frankfurt am Main (DE); Axel Teucher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/994,625

(22) PCT Filed: Dec. 20, 2011

(86) PCT No.: PCT/EP2011/073382
§ 371 (c)(1),
(2), (4) Date: Jun. 14, 2013

(87) PCT Pub. No.: WO2012/084930
PCT Pub. Date: Jun. 28, 2012

(65) Prior Publication Data
US 2013/0261555 A1    Oct. 3, 2013

(30) Foreign Application Priority Data

Dec. 21, 2010 (EP) .................................... 10196227

(51) Int. Cl.
*A61M 5/31*       (2006.01)
*A61M 5/50*       (2006.01)

(52) U.S. Cl.
CPC .......... *A61M 5/3135* (2013.01); *A61M 5/3129* (2013.01); *A61M 5/50* (2013.01); *A61M 5/5086* (2013.01); *A61M 2005/5006* (2013.01); *A61M 2205/273* (2013.01); *Y10T 29/49815* (2015.01)

(58) Field of Classification Search
CPC ... A61M 5/3135; A61M 5/50; A61M 5/3129; A61M 5/5086; A61M 2005/5006; A61M 2205/273; Y10T 29/49815
USPC ................. 604/183, 187, 200–202, 218, 232
See application file for complete search history.

(56) References Cited

U.S. PATENT DOCUMENTS

| | | | |
|---|---|---|---|
| 4,772,271 A |   | 9/1988 | Meyer et al. |
| 5,807,323 A | * | 9/1998 | Kriesel ............. A61M 5/14526 604/232 |
| 5,989,227 A |   | 11/1999 | Vetter et al. |

(Continued)

FOREIGN PATENT DOCUMENTS

| | | |
|---|---|---|
| JP | 2003312675 A | 11/2003 |
| WO | 9916487 A1 | 4/1999 |

(Continued)

*Primary Examiner* — Kevin C Sirmons
*Assistant Examiner* — Amber Stiles
(74) *Attorney, Agent, or Firm* — McDonnell Boehnen Hulbert & Berghoff LLP

(57) ABSTRACT

A drug delivery device for injecting a dose of a medicament, comprising at least one housing component housing a cartridge containing the medicament. The housing component comprises at least one disaggregating means comprising a perforated structure or comprising a structurally weakened portion visibly disposed on the outer circumference of the at least one housing component. The disaggregating means further having at least one bendable and/or pivot-mounted lug adapted as a gripping means and integrally formed with the housing component for dividing the housing component into at least two separate pieces, or for at least partially dividing the housing component into at least two mutually interconnected pieces that can be pivoted with respect to each other.

3 Claims, 2 Drawing Sheets

(56) References Cited

U.S. PATENT DOCUMENTS

2002/0198498 A1* 12/2002 Porat et al. .................. 604/187
2003/0034347 A1* 2/2003 Dewig et al. ................. 220/276
2005/0145628 A1* 7/2005 Schwarz ............ B65D 43/0237
                                                    220/276

FOREIGN PATENT DOCUMENTS

| WO | 0015281 A1 | 3/2000 |
| WO | 2004108194 A1 | 12/2004 |
| WO | 2007143323 A1 | 12/2007 |
| WO | 2008003560 A1 | 1/2008 |

* cited by examiner

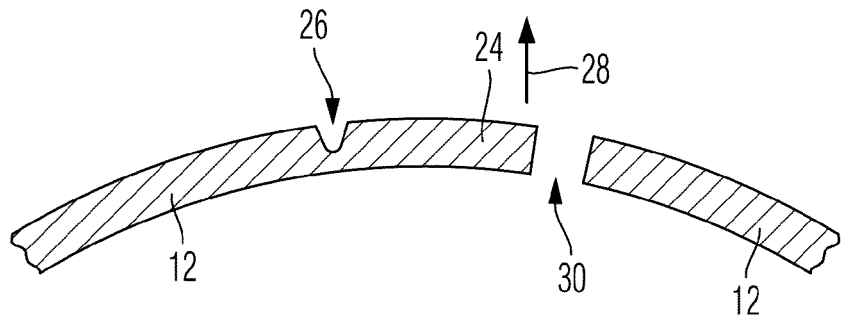
Fig. 3   A - A
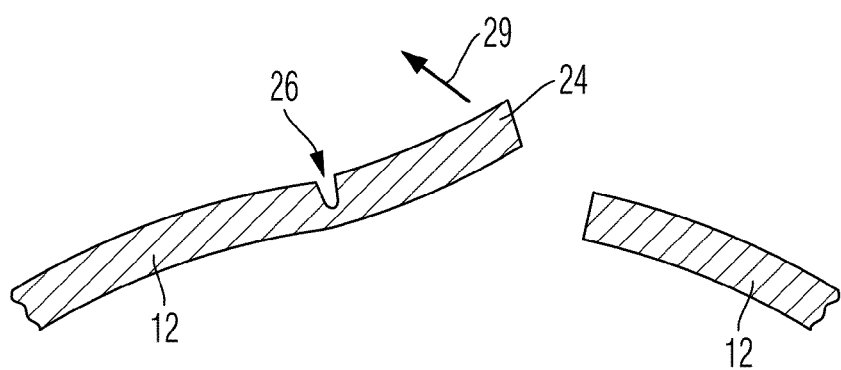
Fig. 4   A - A

DRUG DELIVERY DEVICE WITH HOUSING COMPRISING FRANGIBLE ZONE

CROSS REFERENCE TO RELATED APPLICATIONS

The present application is a U.S. National Phase Application pursuant to 35 U.S.C. §371 of International Application No. PCT/EP2011/073382 filed Dec. 20, 2011, which claims priority to European Patent Application No. 10196227.2 filed Dec. 21, 2010. The entire disclosure contents of these applications are herewith incorporated by reference into the present application.

FIELD OF INVENTION

The present invention relates to a drive mechanism for a drug delivery device that allows a user to select single or multiple doses of an injectable medicament and to dispense the set dosage of the medicament as well as to apply said medicament to a patient, preferably by injection. In particular, the present invention relates to such devices, which are handled by the patients themselves.

BACKGROUND

Drug delivery devices allowing for multiple dosing of a required dosage of a liquid medicinal product, such as liquid medicaments, and further providing administering of the liquid to a patient, are as such well-known in the art.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicament to be administered is provided in a cartridge having a displaceable piston or bung mechanically interacting with a piston rod of a drive mechanism of the drug delivery device. By way of the piston rod, thrust can be applied to the piston in distal direction and a certain amount of the medicinal fluid can be expelled from the cartridge.

Drug delivery devices, such like pen-type injectors further comprise multiple housing components, for instance a cartridge holder adapted to receive a cartridge filled with the medicament as well as a pen body housing or body adapted to receive and to house the drive mechanism which is to be operably engaged with the piston of the cartridge. In particular with disposable pen-type injectors, the entire drug delivery device is intended to be discarded after consumption or after use of the medicament stored in its cartridge.

Since the cartridge is typically made of glass or comparable material being inert to the medicament disposed therein, the cartridge and the housing and/or the functional components of the drug delivery device should be discarded or recycled in separate ways. Proper recycling or discarding of the drug delivery device therefore requires separation of the cartridge from the drug delivery device, which by virtue of its disposable design is not possible, because the drug delivery device is generally not intended or adapted to be disassembled.

It is therefore an object of the present invention to provide a drug delivery device of disposable type which provides an effective means to disassemble or to fractionize at least the housing components of the drug delivery device in order to enable separate recycling of the cartridge and the device components. It is a further object to provide a respective method for fractionizing or for decomposing the disposable drug delivery device in a well-defined and controlled way. Furthermore, it is intended to implement and/or to separate cartridge and device components in a cost-saving and efficient way, e.g. by only introducing minor amendments to the design of existing drug delivery devices.

SUMMARY

The present invention provides a drug delivery device for injection a dose of a medicament. The drug delivery device is typically designed a pen-type injector and comprises at least one housing component which is adapted to house or to receive a cartridge containing the medicament to be dispensed. Furthermore, the housing component may also house or receive a drive mechanism being operably engaged with the cartridge for expelling a dose of the medicament. The cartridge itself typically comprises a vial, carpule or ampoule and has a barrel made of glass or another material being inert to the medicament stored therein.

The barrel is sealed in distal and proximal direction, wherein the cartridge comprises a distal outlet to be connected with a piercing element for dispensing a dose of the medicament. At its opposite end, the cartridge is sealed with a piston slidably disposed in the cartridge. The piston is adapted to become operably engaged with a piston rod of the drive mechanism. By way of the piston rod or drive ram, distally directed pressure can be exerted on the piston, thus inducing a distally directed displacement of the cartridge, leading to a respective pressure built-up in the cartridge, such that a pre-defined amount of the medicament can be expelled therefrom.

The at least one housing component comprises at least one disaggregating means for at least partially dividing the housing component into at least two pieces for gaining access to the cartridge disposed in the housing component. By way of the disaggregating means, the housing component can be separated in at least two pieces, wherein the pieces of the housing component do not have to be entirely separated from each other. It is generally sufficient, when the housing component at least partially disaggregates or disintegrates in such a way, that the at least two housing pieces can be pivoted with respect to each other but remain mutually interconnected.

By at least partially dividing the housing component, it is at least possible to remove the cartridge from the housing and to convey cartridge and housing components of the drug delivery device to separate recycling processes. The disaggregating means is particularly useful with drug delivery devices being designed as disposable after use and that are intended to be discarded once the medicament contained in the cartridge is used up. Since the device is not intended for cartridge replacement, by way of the disaggregating means, the device can be divided and separated into various housing components in a well-defined way, such that reuse of the device is no longer possible. Hence, by making use of the disaggregating means, the device, at least its housing component is substantially destroyed.

According to a preferred embodiment, the drug delivery device comprises a first housing component and a second housing component being inseparably connected with each other. Typically, the first housing component is designed as a body component and the second housing component is designed as a cartridge holder. The body component is intended and adapted to receive and to house a drive mechanism of the drug delivery device, whereas the cartridge holder is adapted and designed to receive a cartridge filled with the medicament to be dispensed.

Cartridge holder and body component are typically connected with each other in a nested, interleaved or intertwined interface portion, in which first and second housing components comprise mutually corresponding receptacle and insert portions. For instance, the distal end of the body component may comprise a receptacle adapted to receive a proximally located insert portion of the cartridge holder. This way, assembly of body component and cartridge holder component requires to insert the cartridge holder component into the receptacle portion of the body component. After mutual engagement of body component and cartridge holder component, the two housing components may be inseparably connected, e.g. by application of heat, for example by way of laser or ultrasonic welding. Once, the assembly process has completed, disassembly of cartridge holder and body component is no longer possible.

In a further preferred aspect, the disaggregating means comprises a structurally weakened portion on the outer surface of the first and/or of the second housing component. By way of the structurally weakened portion, the at least one housing component can be disaggregated in a well-defined way. Preferably, the structurally weakened portion is visibly disposed on the outer circumference of the at least one housing component, thus facilitating the disaggregation process.

In a preferred embodiment, the disaggregating means comprises a perforated structure. By way of a perforation, a disaggregation and division of the at least one housing component into at least two respective housing pieces can be attained. Since the at least one housing component is preferably designed as an injection moulded thermoplastic component, manufacturing of the perforated structure can be implemented without any additional costs or steps of manufacture. Only a respective mould for producing the housing component has to be modified accordingly.

In still another preferred embodiment, the at least one, typically the first and/or the second housing components comprise a substantially cylindrical shape and the perforated or structurally weakened structure extends in circumferential direction. The first and/or the second housing components can therefore be disaggregated along a transverse direction with respect to the longitudinal direction of first and/or second housing components.

Preferably, the disaggregating means, the structurally weakened portion or the perforated structure is arranged outside an interface portion of first and/or second housing components. Thus, by way of the disaggregating means the first and/or second housing components can be disaggregated and divided into at least two pieces while leaving the interconnection of first and/or second housing component intact.

According to another preferred aspect, the disaggregating means comprises at least one bendable and/or pivot-mounted lug adapted as a gripping means. By means of the lug, an effective gripping means is provided allowing a user to strip off the perforated structure, preferably in circumferential direction in order to disaggregate the first and/or the second housing components into at least two pieces.

Since the disaggregating means is preferably integrally formed with the first and/or with the second housing component, when stripping off the gripping means and the perforation provided in or on the first and/or second housing component, the respective housing component can be at least partially disaggregated, at least in such a way that the cartridge can be removed therefrom.

According to another preferred aspect, the pivot- or bending axis of the lug extends substantially parallel or perpendicular to the longitudinal axis of the first and/or second housing components. In particular, when the perforation extends in circumferential direction, the pivot- or bending axis of the lug extends substantially parallel to the longitudinal axis of the first and/or the second housing component. This way, stripping off the perforation starts with lifting of the bendable or pivot-mounted lug and a tearing apart of the perforation simply follows in the course of the initial lifting procedure.

In still another preferred aspect, the lug or free end of the perforated structure substantially flushes with the outer circumference of the first and/or second housing component. This way, unintentional gripping of the lug can be effectively prevented.

Moreover, and according to a further preferred embodiment, the disaggregating means and/or its lug is covered with an adhesive cover or foil. This way, disaggregation or disintegration of the first and/or second housing components can be effectively inhibited. On the one hand, the bendable or pivot-mounted lug cannot be lifted or gripped and on the other hand, by way of the adhesive foil, the perforated or structurally weakened structure is at least slightly structurally stiffened.

In still another aspect, the drug delivery device is readily equipped with a cartridge positioned and fixed by the cartridge holder, wherein the cartridge is at least partially filled with the medicament to be dispensed. Moreover, the drive mechanism is already operably engaged with the piston of the cartridge when the drug delivery device is delivered to the end-customer.

Finally, the various components of the drug delivery device, in particular its cartridge and its housing or the functional components of its drive mechanism are intended to be separately discarded after consumption or use of the medicament.

By making use of the disaggregating means, the drug delivery device can be disassembled and fractionized, such that at least the cartridge, typically comprising a glass barrel can be removed from the cartridge holder and can be discarded or recycled separately.

In still another and independent aspect, the invention further relates to a method of disaggregating or fractionizing a drug delivery device after its use, wherein the drug delivery device comprises at least one housing component having a disaggregating means, by way of which the housing component can be disaggregated. In particular, the method is applicable to a drug delivery device as described above.

The method of fractionizing the drug delivery device comprises the steps of at least partially dividing the housing component into at least two pieces by means of the disaggregating means for gaining access to the cartridge disposed in the cartridge holder. Thereafter, the cartridge is removed from the cartridge holder and is discarded or recycled separately from the housing or functional components of the drug delivery device.

This way, even a disposable drug delivery device, such like a pen-type injector intended to be discarded after usage can become subject to an environmentally friendly discarding- or recycling process.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca1+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in greater detail by making reference to the drawings, in which:

FIG. 3 illustrates a cross section along A-A according to FIG. 2 prior to a disaggregating procedure and FIG. 4 shows the cross section according to FIG. 2 during a disaggregating procedure.

DETAILED DESCRIPTION

Figure 1:
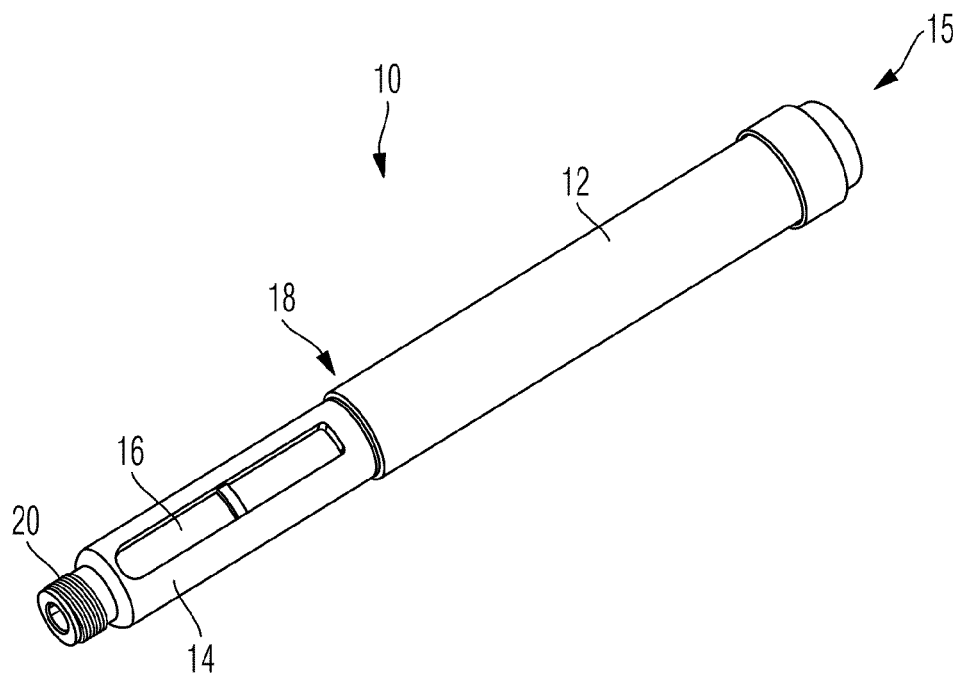
FIG. 1 shows a drug delivery device of pen-type injector in a perspective illustration.

The drug delivery device 10 as depicted in FIG. 1 comprises a pen body housing 12 connected with a cartridge holder section 14, in which a cartridge 16 is disposed. In the illustrated sketch, the cartridge 16 is only visible through an inspection window provided in the cartridge holder 14. The cartridge holder 14 at its distal end section comprises a threaded socket 20 adapted to receive a correspondingly threaded needle assembly having an injection needle intended to pierce a distally located sealing member of the cartridge 16, which is typically designed as a septum.

Opposite its distal outlet, the cartridge 16 comprises a displaceable piston to operably engage with the piston rod or drive ram of a drive mechanism that is housed in the body 12. Body 12 and cartridge holder 14 are interconnected by forming an interface 18 in an interleaved and mutually overlapping manner.

In the illustrated embodiment, the distal end of the body 12 comprises a receptacle adapted to receive a proximally located but not explicitly illustrated insert portion of the cartridge holder 14. Furthermore, at a proximal end of the body 12, a dose button 15 is located allowing to manipulate and to control dose setting and dose dispensing of the drug delivery device 10.

Figure 2:
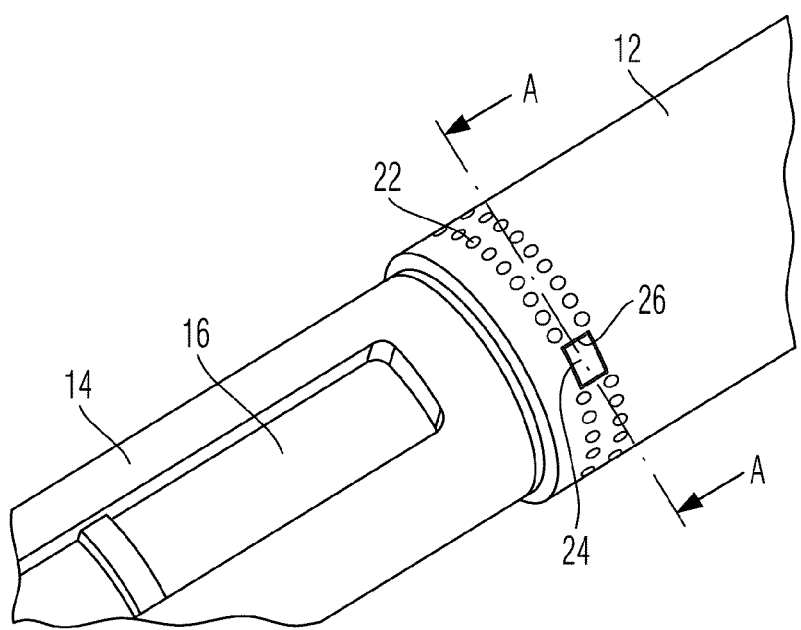
FIG. 2 shows an enlarged sectional view of the drug delivery device according to FIG. 1.

In FIG. 2, the interface section 18 of pen body housing 12 and cartridge holder 14 is illustrated in a magnified view. As shown there, the body housing component 12 comprises an annular or circumferential perforated structure 22 which enables disaggregation of the body 12 into at least two pieces. As illustrated in FIG. 2, the disaggregating means of the body component 12 comprises two axially separated perforations as indicated by the circumferentially aligned circles or dots.

This way, an annular perforated strip can be torn off for disaggregating the body component 12.

In FIGS. 3 and 4 a section of the perforated structure 22 is illustrated in cross section along A-A according to FIG. 2. There, the strip to be torn off comprises a lug 24 integrally formed with the cylindrical housing component 12 of the drug delivery device 10. The free end of said lug 24 can be gripped by inserting a fingernail or a comparable tool into a slit 30, thus allowing to lift up the pivoting or bendable lug 24 in a radially outwardly pointing direction 28. The lug portion 24 is separated from the body component 12 by a groove 26 defining a pivot or bending axis for the gripping or lifting procedure of the lug 24.

As soon as the free end of the lug 24 has been lifted as depicted in FIG. 2, the direction of tearing 29 typically points in a rather circumferential direction in order to tear the perforation and the body apart.

Even though not explicitly illustrated, the perforated structure or the disaggregating means, in particular the pivot-mounted lug 24 can be covered with an adhesive foil or cover during conventional use of the drug delivery device. For the purpose of disaggregating the housing 12, 14 of the drug delivery device 10, the protective foil has to be removed prior to get access to the gripping end of the lug 24. It is also conceivable, that the adhesive cover or foil remains sticked with the outer surface of the pivot-mounted lug 24 in order to facilitate or to support its lifting up.

Additionally, it is to be mentioned, that the perforation as depicted in FIG. 2 may be designed as an annular strip entirely surrounding the outer circumference of the pen body housing 12. Alternatively, it may be even sufficient, when the perforation does not entirely extend around the body's 12 outer circumference. An annular extension of about 270° to 350° around the annular body 12 may already be sufficient to provide cartridge removal. This way, disaggregating of the body component 12 does not require a complete separation and dividing of the housing component 12. It may be sufficient, when the distal end or the interface portion 18 can be folded away with respect to the body component 12 in order to gain access to the cartridge 16 disposed in the cartridge holder 14.

Apart from that, the disaggregating means and its corresponding housing component 12, 14 should be designed such that at least the cartridge 16 can be removed from the cartridge holder 14 once the disaggregating means 22, 24 has been activated.

The invention claimed is:

1. A drug delivery device for injecting a dose of a medicament, comprising:
    a cartridge holder housing a cartridge containing the medicament,
    a body component,
    wherein the cartridge holder comprises a threaded socket at a longitudinal distal end section to engage with a correspondingly threaded needle assembly with an injection needle to pierce a distally located sealing member of the cartridge,
    wherein the cartridge holder and the body component are inseparably connected with each other,
    wherein the body component comprises at least one disaggregating means comprising a perforated structure or comprising a structurally weakened portion visibly disposed on the outer circumference of the body component, the disaggregating means further having at least one bendable and/or pivot-mounted lug adapted as a gripping means and integrally formed with the body component
    (i) for dividing the body component into at least two separate pieces, or
    (ii) for at least partially dividing the body component into at least two mutually interconnected pieces that can be pivoted with respect to each other
    for gaining access to the cartridge disposed in the cartridge holder and to enable removal of the cartridge from the cartridge holder, wherein
    the body component comprises a substantially cylindrical shape wherein the lug flushes with the outer circumference of the body component and wherein a free end of the lug is separated from the body component by a slit configured to receive a fingernail or a comparable tool for lifting up of the lug in a radially outwardly pointing direction, wherein the free end of the lug flushes with the outer circumference of the body component, and
    wherein a groove defining a pivot or bending axis is located between the lug and the body component and
    wherein the pivot or bending axis extends substantially parallel to a longitudinal axis of the body component.

2. The drug delivery device according to claim 1, wherein the cartridge holder is equipped with a cartridge filled with the medicament.

3. A method of disaggregating a drug delivery device according to claim 1 after its use, comprising the steps of:
    (i) dividing the body component into at least two separate pieces, by means of a disaggregating means for gaining access to the cartridge disposed therein, or
    (ii) at least partially dividing the body component into at least two mutually interconnected pieces that can be pivoted with respect to each other by means of a disaggregating means for gaining access to the cartridge therein,
    removing the cartridge from the body component and discarding the cartridge separate from the body components of the drug delivery device.

* * * * *